(12) United States Patent
Albarella et al.

(10) Patent No.: US 6,187,268 B1
(45) Date of Patent: Feb. 13, 2001

(54) TRANSPARENT FLOW THROUGH MEMBRANE FOR DRY REAGENT ANALYTICAL DEVICES

(75) Inventors: James P. Albarella, Granger, IN (US); Karl-Heinz Hildenbrand, Krefeld (DE); Spencer H. Lin; Michael J. Pugia, both of Granger, IN (US); LLoyd S. Schulman, Osceola, IN (US)

(73) Assignee: Bayer Corporation, Elkhart, IN (US)

( * ) Notice: Under 35 U.S.C. 154(b), the term of this patent shall be extended for 0 days.

(21) Appl. No.: 09/405,116

(22) Filed: Sep. 27, 1999

Related U.S. Application Data

(63) Continuation of application No. 09/123,225, filed on Jul. 27, 1998, now abandoned.

(51) Int. Cl.[7] .............................. C12Q 1/68; G01N 33/53; G01N 31/22; G01N 33/70; G01N 33/00
(52) U.S. Cl. ................................ 422/57; 422/56; 422/57; 422/58; 422/52; 422/68.1; 435/6; 435/7.91; 435/7.92; 435/28; 435/962; 435/975; 435/969; 435/970; 435/287.1; 435/287.2; 435/287.8; 435/287.9; 436/518; 436/525; 436/533; 436/534; 436/540; 436/541; 436/805; 436/810; 436/28; 436/169; 436/170; 436/172; 436/164

(58) Field of Search .................... 435/287.1, 6, 287.2, 435/7.91, 287.7, 7.92, 287.8, 28, 287.9, 7.5, 865, 810, 970, 962, 7.94, 969; 436/28, 196, 87, 164, 169, 170, 518, 531, 533, 534, 805, 810, 172, 541, 525, 540; 422/56–58, 52, 68.1

(56) References Cited

U.S. PATENT DOCUMENTS

| | | | |
|---|---|---|---|
| 5,141,850 | * | 8/1992 | Cole et al. ............................. 436/525 |
| 5,736,335 | * | 4/1998 | Emmons et al. ........................ 435/6 |
| 5,801,061 | * | 4/1997 | Stephenson et al. ................ 436/169 |

OTHER PUBLICATIONS

J. Gosling, A Decade of Development in Immunoassay Methodology, Clin. Chem. 36 (8): 1408–1427 (1990).*

* cited by examiner

Primary Examiner—Long V. Le
Assistant Examiner—Gailene R. Gabel
(74) Attorney, Agent, or Firm—Jerome L. Jeffers

(57) ABSTRACT

Disclosed is a diagnostic device for the colorimetric detection of an analyte in a test fluid. The device is a dry reagent layer which is overcoated with a transparent, fluid permeable membrane. The membrane is made up of a combination of a water dispersible and a water soluble polymer. The membrane may contain a surfactant and a thickener.

5 Claims, No Drawings

TRANSPARENT FLOW THROUGH MEMBRANE FOR DRY REAGENT ANALYTICAL DEVICES

This is a continuation of application Ser. No. 123,225, filed Jul. 27, 1998, now abandoned.

BACKGROUND OF THE INVENTION

Dry reagent analytical devices typically involve absorbent pads in which there are disposed reagent systems which react with analytes in fluid test systems applied to the device to provide a detectable response. Certain of these devices involve an enzymatic reaction with the analyte in the presence of a peroxidase and a hydroperoxide to cause a detectable color change in a redox dye. These systems are normally based on the use of filter paper as the absorbant pad. Other such devices operate on the basis of immunoreactivity of a labeled antibody located in the reagent device which specifically binds with analyte in the test sample to provide a detectable response in a specified region of the test device. Nitrocellulose is a preferred base material for this sort of device due to its flow through properties.

These dry reagent devices are inexpensive and convenient to use but suffer from certain limitations. For example in the analysis of serum for the mb isoform of creatine kinase (CKMB) there has been observed poor immunochemical separation, i.e. the ability of antibodies to capture the analyte of choice without non-specific binding. The slower the separation, the more time analytes have to be captured. With faster separation there is a limited time for the reaction to take place. Dry reagent tests for urine creatinine sometimes exhibit instability due to incompatible chemicals.

There are many examples of incompatible chemicals in dry reagent systems. For example, the base in white blood cell reagents causes premature hydrolysis of protease substrate, iron in occult blood reagents causes premature oxidation of redox dye indicators to their colored form which is also the result of the presence of iodate in glucose reagents. In the case of copper based tests for creatinine, the copper can oxidize redox indicators such as tetramethylbenzidine to their colored form in the absence of creatinine.

Tests for occult blood in urine can be skewed by the presence of ascorbate in the urine test sample which acts as a reducing agent causing false negative results and urine protein tests can be rendered inaccurate by the presence of buffers in the urine sample being tested. Dry assay devices for determining white blood cells in urine can be influenced by interference due to proteins in the urine sample and whole blood assays, such as blood glucose and blood CKMB, suffer from interference caused by red blood cells. The present invention provides a means for alleviating these problems by overcoating the dry reagent device with a permeable transparent membrane.

Previous methods for dealing with these problems have involved separating the reagents into discrete, stacked layers. There are, however, problems associated with the use of the discrete, stacked layer configuration. Thus, the top layer(s) must allow the test sample and analyte to pass to the lower layers while continuing to separate certain interfering chemicals and/or biochemicals. For example, metals such as copper or iron should be separated from redox indicators and bases from protease substrates. Oxidants such as iodate and reductants such as ascorbate need to be separated from redox indicators such as tetramethylbenzidine. In addition, the top layer must be translucent to permit reading of the signal produced in the bottom layer. Nylon mesh and glass fiber paper are among the materials used as semitransparent, discrete layers. The use of these materials requires formats to hold the layers together, which formats are typically difficult to manufacture, do not provide complete contact between the layers and may not effectively prevent migration of reagents between the layers.

There are various diffusible, adhesive compositions which can be used to secure two layers in integrated, multilayered reagent devices. In U.S. Pat. No. 5,110,550 there is described an absorbent covering layer which is non-transparent until liquid is transported from a color forming area. In U.S. Pat. No. 3,992,158 a transparent support at the bottom layer of a multiple stack of layers is described. The support layer is not permeable, so this type of device is read from the bottom. U.S. Pat. No. 4,587,099 describes the use of a transparent plastic netting which is fixed to a polystyrene strip handle which serves to hold the reagent layers together. The device is read from the top and the netting is permeable. However, the permeable layer is not attached to the underlying reagent layer.

U.S. Pat. Nos. 4,806,311 and 4,446,232 describe the advantages of the use of multilayered reagent devices for carrying out immunoassays and in U.S. Pat. No. 4,824,640 there is disclosed a transparent reagent layer for analytical reagents which consists of a water soluble or water swellable component and an essentially water insoluble film forming component.

SUMMARY OF THE INVENTION

The present invention involves a diagnostic device for the colorimetric detection of an analyte in a test fluid comprising a dry reagent layer overcoated with a transparent, fluid permeable water swellable membrane. The basic elements of the transparent membrane are an essentially water insoluble polymeric dispersion and a water soluble polymer. The layer's fluid permeability can be adjusted by modifying the ratio of polymer dispersion to the water soluble component. Preferably included in the membrane formulation are a surfactant to help the dispersion attain wettability and spreadability, and a thickener such as silica gel. The transparent layer is cast from its aqueous dispersion/solution to form the fluid permeable membrane upon evaporation of the aqueous carrier.

DESCRIPTION OF THE INVENTION

The basic elements of the transparent, fluid permeable membrane involve an aqueous based polymer dispersion and a water soluble polymer. The permeability of the membrane can be adjusted by varying the ratio of the polymer dispersion to the water soluble component. Typically, this ratio will range from 50:1 to 1:1 on a w/w basis with a ratio of 10:1 to 5:1 with an excess of the film forming polymer dispersion being preferred. An increase in the water dispersible polymer will increase the membrane's permeability which is desirable when faster flow is desired. Conversely, increasing the concentration of the water soluble polymer will decrease the membrane's permeability in cases where greater contact, and accordingly more mixing of the reagents, is desired. These layers are particularly useful in conjunction with diagnostic dry reagent test devices because they allow penetration of the analyte present in the fluid test sample through the membrane so that it comes into contact with the reagent layer which remains transparent to facilitate any color change being read from the top of the device.

Polyurethane dispersions are preferred for use as the dispersible polymer due to their adhesive properties, flexibility and structural diversity. The reaction of a diisocyanate with equivalent quantities of a bifunctional alcohol provides a simple linear polyurethane. These products are unsuitable for use in the manufacture of coatings, paints and elastomers. When simple glycols are first reacted with dicarboxylic acids in a polycondensation reaction to form long chain polyester-diols and these products, which generally have an average molecular weight of between 300 and 2000, are subsequently reacted with diisocyanates the result is the formation of high molecular weight polyester urethanes. Polyurethane dispersions have been commercially important since 1972. Polyurethane ionomers are structurally suitable for the preparation of aqueous two phase systems. These polymers, which have hydrophilic ionic sites between predominantly hydrophobic chain segments are self-dispersing and, under favorable conditions, form stable dispersions in water without the influence of shear forces and in the absence of dispersants. In order to obtain anionic polyurethanes, such as BAYHYDROL DLN, which are preferred for use in the present invention, diols bearing a carboxylic acid or a sulfonate group are introduced and the acid groups are subsequently neutralized, for example with tertiary amines. Sulfonate groups are usually built via a diaminoalkanesulfonate, as these compounds are soluble in water. The resulting polyurethane resins have built in ionic groups which provide mechanical and chemical stability as well as good film forming and adhesion properties.

Cationic polyurethane dispersions such as PRAESTOL E 150 from Stockhausen Chemical Co. may also be used in forming the membrane. One method of preparing cationic polyurethanes is by the reaction of a dibromide with a diamine. If one of these components contains a long chain polyester segment, an ionomer is obtained. Alternatively, polyammonium polyurethanes can be prepared by first preparing a tertiary nitrogen containing polyurethane and then quaternizing the nitrogen atoms in a second step. Starting with polyether based NCO prepolymers, segmented quaternary polyurethanes are obtained.

The most important property of polyurethane ionomers is their ability to form stable dispersions in water spontaneously under certain conditions to provide a binary colloidal system in which a discontinuous polyurethane phase is dispersed in a continuous aqueous phase. The diameter of the dispersed polyurethane particles can be varied between about 10 and 5000 nm. Polyurethane dispersions which are ionic with the ionic radicals being sulphonate, carboxylate or ammonium groups are particularly suitable.

Also suitable for use in the present invention are other film forming polymer dispersions such as those formed by polyvinyl or polyacrylic compounds, e.g. polyvinylacetates or polyacrylates, vinyl copolymers, polystyrenesulfonic acids, polyamides and mixtures thereof. By combining the polymer dispersion with a water soluble polymer there is formed a matrix which forms a swellable network like web. The tighter the web, the smaller the pores and the slower the flow of the test fluid through the matrix. As water soluble polymers the known polymers such as, for example, polyacrylamides, polyacrylic acids, cellulose ethers, polyethyleneimine, polyvinyl alcohol, copolymers of vinyl alcohol and vinyl acetate, gelatine, agarose, alginates and polyvinylpyrrolidone are suitable. This second polymer component is sometimes referred to as the swelling component due to its swellability by absorbing water. Polyethyleneoxides, polyvinylpyrrolidones and polyvinylalcohols are preferred. These polymers can vary widely in molecular weight so long as they are water soluble and miscible with the aqueous polymer dispersion. Polyethylene oxides of a molecular weight from 300,000 to 900,000 g/mol and polyvinylpyrrolidone having a molecular weight of from 30,000 to 60,000 g/mol are particularly suitable. The molecular weight of the water soluble polymer is not critical so long as they are miscible with the polymer dispersion and allow the incorporation of assay specific reagents such as buffers, indicators, enzymes and antibodies. The finished film should be swellable so as to be permeable to the test fluid.

The polymers are dispersed/dissolved in a solvent (preferably aqueous) preparatory to its application to the surface of the dry reagent device by use of a dispenser as in the following examples. In the preferred aqueous casting solutions, aqueous polymer dispersions are mixed with an aqueous solution of the second polymer such as, for example, polyvinyl acetate dispersions with cellulose ethers, polyurethane dispersions with polyvinyl alcohol, polyurethane dispersions with gelatine or polyurethane dispensions with polyvinylpyrrolidone. Normally, a surfactant is added to the formulation to enhance its spreadability and a thickener such as silica gel is added to thicken the formulation to a consistency which facilitates its being spread across the surface of the reagent device. The formulation is then applied to the surface of the dry reagent device, such as by a Myer rod applicator or a wiped film spreader, and dried to remove solvent. Typical dry thicknesses of the permeable membrane range from 5 to 20 mils.

Once in place, the permeable membrane can serve as a filter for removing red blood cells from whole blood test samples thereby avoiding the interference with reading the colored response in the reagent layer. Protein interference in an assay for white blood cells in urine is alleviated by the protein sticking to the membrane and not passing through the reagent and buffer interference in tests for urine protein is reduced by either adhering to the membrane (ion pairing) or being neutralized (proton exchange) with the result being either that the buffer does not come into contact with the reagent or is altered to a noninterferring form which matches the pH of the reagent. The instability of reagents for testing urine creatinine due to the presence of incompatible chemicals in the urine sample is reduced by the permeable membrane since the membrane can be fabricated to hold a capture reagent such as copper bonded to a charged polymer. The capture reagent keeps creatinine separated from the redox indicator until it comes into contact with the fluid test sample. The sample presents creatinine to bind with the copper and the copper is liberated from the polymer.

Ascorbate interference with urine occult blood tests can be alleviated by incorporating ascorbate scavengers, such as a metal capable of oxidizing ascorbate bound to a polymer, into the membrane formulation. Polymer bound metal ascorbate scavengers are described in U.S. Pat. No. 5,079,140. Other oxidizing agents such as iodate and persulfate can be immobilized within the porous membrane to serve as ascorbate scavengers.

The permeable membrane of the present invention can be used advantageously in conjunction with immunoformats to provide sensitive assays for various analytes. For example, a transparent membrane according to the present invention can be prepared with an immobilized anti-binding label antibody contained therein. Typically, this antibody will be immobilized within the membrane by attaching it to a larger entity such as a latex particle which is incorporated into the polymer blend which forms the membrane before it is cast onto the reagent device. Thus, when the binding label on the anti-analyte antibody has the fluorescein structure, such as in the case of fluorescein isothiocyanate (FITC), anti-FITC can be interspersed in the permeable membrane to capture FITC labeled anti-analyte antibody. In addition, anti-analyte antibody labeled with a peroxidase is incorporated into the membrane, so that as test fluid flows through the membrane analyte contained therein will bind with bound anti-analyte antibody and peroxidase labeled anti-analyte antibody to form a sandwich attached to the membrane thereby preventing the peroxidase from reaching the reagent layer, which contains a peroxide and a redox dye, and providing a colored response. In this embodiment, the response produced by the interaction of the analyte, peroxidase, peroxide and redox dye is inversely proportional to the concentration of the analyte in the fluid test sample.

The present invention is further illustrated by the following examples:

EXAMPLE I

A transparent membrane was produced on top of a reagent strip for albumin comprising a filter paper substrate prepared as outlined in the following table:

| Ingredient | Function | Pref Conc Used | Allowable Range |
|---|---|---|---|
| Protein Reagent Composition | | | |
| 1st Application | | | |
| Water | Solvent | 1000 mL. | — |
| Tartaric Acid | Canon Sensing Buffer | 93.8 g (625 mM) | 50–750 mM |
| Quinaldine red | Background dye | 8.6 mg (12 µM) | 5–30 µM |
| 2nd Application | | | |
| Toluene | Solvent | 1000 mL | — |
| DIDNTB | Buffer | 0.61 g (0.6 mM) | 0.1–3.0 mM |
| Lutonal M40 | Polymer enhancer | 1.0 g | 0.5–4 g/L |

DIDNTB = 5',5"-Dinitro-3',3"-Diiodo-3,4,5,6-Tetrabromophenolsulfonephthalein

The transparent membrane was prepared as follows:

1) To a 250 ml steel beaker using a propeller stirrer as dissolver was added 75 g buffer (pH 7.0, 50 nM phosphate mono basic) and 0.5 g Pluronic P75, a propylene oxide/propylene glycol surfactant from BASF. Under stirring there was slowly added 0.3 g octanol followed by 5.0 g of Aerosil 200 fumed silica gel as thickener. The stirrer was adjusted to 2000 rpms for several minutes to allow for complete dispersion.

2) Under stirring there was added 40.25 g of a 40% aqueous dispersion of BAYHYDROL DLN (water dispersible polyurethane) from Bayer AG followed by 0.2 g of polyethyleneoxide (PEO) 900,000 MW with continued stirring for about 15 minutes.

3) The resulting coating solution was then cast onto an albumin reagent strip described above to a wet thickness of 250 µm. The combined membrane and reagent were dried at 90° C. for 5 minutes.

The protein reagent was developed by applying a solution either containing or lacking albumin. The membrane exhibited good flow through properties and the color formed in the albumin reagent was clearly visible as demonstrated in Table 1 wherein the reflectance changed from 98.8% to 44.2% after applying water to the dry reagent. The application of water caused a color change because it dissolved buffer in the reagent and the color of the reagent is dependent on pH. The change was the same with or without the membrane.

The effect of buffer, i.e. pH 9.0 Fisher Buffer containing 100 mM boric acid, potassium chloride and sodium chloride, was prevented with the transparent membrane as indicated by the lack of any difference in reflectance between water and buffer with the membrane. Without the membrane, a large false positive shift in reflectance from 41.0% to 15.6% occurred after applying buffer to the dry reagent due to the elevation of the pH by the buffer which caused the protein indicator to change color. The membrane also included charged polymers (BAYHYDROL DLN) which helped to buffer the sample.

The membrane used in this example exhibited no protein separating ability; the albumin response, elicited using a 50 mg/dL human serum albumin in water, of the reagent was not affected by the transparent membrane as indicated by the reflectance of 6.84% with and 5.6% without the membrane. Hence, the membrane was completely transparent and did not reduce the reflectance of color. The membrane was also more uniform in color than the reagent without the membrane. The results of this experiment are set out in Table 1.

TABLE 1

Demonstration of flow through, color, visibility and buffering properties:

| | % Reflectance at 610 nm & 1 minute | | | |
|---|---|---|---|---|
| | dry | wet | buffer | albumin |
| Albumin reagent without transparent membrane | 98.0 | 41.0 | 15.6 | 6.84 |
| Albumin reagent with transparent membrane | 98.8 | 42.2 | 44.9 | 5.55 |

It is possible to cast the membrane onto any surface including filter paper, glass paper and woven polymer fibers.

EXAMPLE II

Another transparent membrane composition was cast on top of a protein reagent as described in Example I which also included hydrogen peroxide and phenylenediamine as an ascorbate detecting reagent. A membrane capable of removing ascorbate interference was prepared as follows:

1) 10 mL of copper sulfate (10 mM) mixed with 1.0% aqueous poly(acrylic acid) having a molecular weight of 750,000 g/mol was added to the coating solution of Example I. The resulting solution was stirred until completely dispersed.

2) The coating solution was then cast onto a dry reagent prepared by saturating Alhstrom 205C paper with an ethanol solution containing 25 mM N,N-Bis(2-hydroxyethyl)-1,4-phenylenediamine sulfate monohydrate as redox indicator and 25 mM diisopropylbenzene dihydroperoxide to a thickness of 250 µm. The combined membrane and reagent were dried at 90° C. for 5 minutes.

The ability of the membrane to remove ascorbate interference is demonstrated in Table 2, the data for which were generated by applying an aqueous solution with and without ascorbate to the membrane surface. Referring to Table 2, the color of the ascorbate indicator reagent was reduced by ascorbate from 29.3% to 74.1% without the membrane but was not reduced in the case in which the reagent bore the membrane thereby indicating that the membrane removed ascorbate/interference from the test solution.

TABLE 2

Demonstration of Ascorbate Scavenging Properties

| | % Reflectance @ 550 nm/1 minute | |
|---|---|---|
| | wet | ascorbate |
| Redox reagent without membrane | 29.3 | 74.1 |
| Redox reagent with membrane | 15.8 | 28.4 |

The membrane composition included copper sulfate and aqueous poly(acrylic acid). The copper sulfate metal ($Cu^{++}$) bound to the polyacrylic acid exchange resin and oxidized the ascorbate. As disclosed in U.S. Pat. No. 5,079,140; any metal capable of oxidizing ascorbate can be used with any polymer capable of binding the metal ion. In addition, other oxidizing agents such as iodate and persulfate can be used as long as they are capable of being immobilized within the membrane.

EXAMPLE III

A transparent membrane, capable of immobilizing an antibody attached to a latex particle, was produced as follows:

1) using a disperser and a 250 ml steel beaker the following procedure was carried out: weigh in 150 g of Pierce Casein Blocker (pH 7.4) buffer to prevent any non-specific protein binding to the membrane and 1.0 g of Pluronic L64 surfactant. Under slow stirring 0.6 g of octanol was added followed by 12.0 g of Aerosil 200. This was followed by stirring for several minutes at 2000 rpms for complete dispersion.

2) under stirring there was added 110.0 g of a 40% aqueous solution BAYHYDROL DLN followed by 0.4 g of PEO 900,000 with continued stirring for about 15 minutes.

3) 300 $\mu$L of an ant-fluorescein isothiocyanate (FITC) latex particle suspension was added to 3.0 g of the transparent membrane precursor and vortexed. The particles used in this experiment were white with an average particle diameter of 0.3$\mu$.

4) The solution was then cast onto a wicking pad (Whatman 31ET) using a 15 mil wet film applicator. The combined transparent membrane and wicking pad were dried in a convection oven at 40° C. for 20–30 minutes.

The transparent membrane coated onto the piece of wicking paper acts as a generic capture layer for a specifically labeled antigen in which the antibody retains its immunological activity. The example demonstrates usage of a sandwich assay in which anti-FITC was adsorbed onto latex particles. The resulting suspension, which served as a capture antibody, was added to the transparent membrane dispersion, vortexed and then cast onto the wicking paper and dried. Triplicate normal human serum test samples with various analyte concentrations (CKMB in this example) were produced: 0 ng/mL, 50 ng/mL and 150 ng/mL. Anti-CKMB labeled horseradish peroxidase and anti-CKMB labeled FITC were added to the samples for sandwich formation. Each sample (8 $\mu$L) was added to the transparent membrane and allowed to soak into the wicking pad which was followed by a 0.1 mg/mL solution of tetra methylbenzidine (TMB) redox indicator spiked with 2 $\mu$L/mL of 3% hydrogen peroxide. Since the 0 ng/mL sample contained no analyte, no sandwich was formed and the highest reflectance signal resulted. As shown in Table 3, a sample with no analyte present had the highest reflectance with decreasing reflectance as the analyte increased.

TABLE 3

Demonstration of Immunoassay with Transparent Membrane

% Reflectance using the blue filter on a CLINITEK ™ 50 reflectance spectrometer:

| 0 ng/ml CKMB | 50 ng/nL CKMB | 150 mg ng/mL CKMB |
|---|---|---|
| 67% | 60% | 48% |

The anti-CKMB, horseradish peroxidase (HRP) and anti-CKMB/FITC were mixed together whereupon the serum sample containing CKMB was added to the two antibodies to form a sandwich with the analyte. The anti-FITC was attached to the latex to immobilize it onto the transparent membrane. As anti-CKMB labeled HRP/CKMB/anti-CKMB sandwiches flowed through the transparent membrane, they attached to anti-FITC latex by way of the FITC label on the anti-CKMB which was immobilized on the transparent membrane. Anything that did not attach flowed through onto the wicking pad. By adding tetramethylbenzidine to the membrane as substrate for the horseradish peroxidase there was produced a colored response, the intensity of which was in direct proportion to the CKMB concentration, i.e. less reflection as the color became darker.

What is claimed is:

1. A test device for colorimetric determination of an analyte in a test fluid which device comprises a dry reagent layer containing a hydroperoxide and a redox dye capable of colorimetrically detecting the presence or concentration of the analyte which dry reagent layer is overcoated with a transparent, fluid permeable, swellable membrane comprising a blend of an aqueous based dispersion of water dispersible polyurethane together with water soluble polyethyleneoxide, polyvinylpyrrolidone or polyvinylalcohol wherein the transparent, fluid permeable, swellable membrane has immobilized therein an anti-fluorescein antibody and contains a first mobile anti-analyte antibody bearing fluorescein and a second mobile peroxidase labeled anti-analyte antibody together with copper bonded to a charged polymer as a capture reagent for creatinine in the test fluid, so that when the analyte is present in the test fluid there is formed a fluorescein labeled anti-analyte antibody/analyte/peroxidase labeled anti-analyte antibody sandwich in which the fluorescein and peroxidase are available for further reaction and are captured by interaction with the immobilized anti-fluorescein antibody, so that analyte in the test fluid will prevent the peroxidase labeled anti-analyte antibody from flowing through the transparent, fluid permeable, swellable membrane to the dry reagent layer and, in the absence of analyte in the test fluid, the peroxidase labeled anti-analyte antibody will flow through the transparent, fluid permeable, swellable membrane to the dry reagent layer where the peroxidase from the peroxidase label on the second anti-analyte antibody can react with the hydroperoxide and redox dye to colorimetrically detect the analyte wherein the intensity of the color formed by the colorimetric determination reaction is in an inverse relationship to the concentration of the analyte in the test fluid.

2. The device of claim 1 wherein the fluorescein is fluorescein isothiocyanate.

3. A method for determining the presence or concentration of an analyte in a fluid test sample which comprises contacting the device of claim 1 with the fluid test sample and correlating a color change in the reagent layer with the presence or concentration of the analyte.

4. The method of claim 3 wherein the dry reagent layer is pretreated with the hydroperoxide and the redox dye so that they are absorbed therein.

5. The method of claim 3 wherein the fluid test sample is combined with the first anti-analyte antibody and the second anti-analyte antibody before it is contacted with the device.

* * * * *